| United States Patent [19] | [11] Patent Number: 4,914,256 |
|---|---|
| Rodewald | [45] Date of Patent: Apr. 3, 1990 |

[54] REACTIVATION OF PARTIALLY DEACTIVATED CATALYST EMPLOYING ULTRASONIC ENERGY

[75] Inventor: Paul G. Rodewald, Rocky Hill, N.J.

[73] Assignee: Mobil Oil Corp., New York, N.Y.

[21] Appl. No.: 213,801

[22] Filed: Jun. 30, 1988

[51] Int. Cl.$^4$ .......................... C07C 2/58; B01J 37/34; B08B 3/12
[52] U.S. Cl. ........................................ 585/726; 134/1; 204/157.62; 204/158.14; 208/111; 208/120; 208/140; 502/5; 502/31; 502/522; 585/953
[58] Field of Search .................. 502/5, 31, 53, 56, 20, 502/22, 522; 204/157.42, 157.62; 585/953, 726; 134/1

[56] References Cited

U.S. PATENT DOCUMENTS

| 2,578,377 | 12/1951 | Smith | 204/157.62 |
|---|---|---|---|
| 2,742,408 | 4/1956 | La Porte | 204/157.62 |
| 2,800,444 | 7/1957 | Hughes et al. | 204/157.62 |
| 3,231,513 | 1/1966 | Graves et al. | 134/1 |
| 3,245,892 | 4/1966 | Jones | 204/157.42 |
| 3,505,207 | 4/1970 | Haney et al. | 502/30 |
| 3,976,714 | 8/1976 | Rodewald | 585/726 |
| 4,062,696 | 12/1977 | Ducote | 502/516 |
| 4,083,885 | 4/1978 | Rodewald | 585/726 |
| 4,086,184 | 4/1978 | Henry et al. | 502/5 |

*Primary Examiner*—Paul E. Konopka
*Attorney, Agent, or Firm*—Alexander J. McKillop; Charles J. Speciale; Dennis P. Santini

[57] ABSTRACT

A solid catalyst composition which has undergone a partial loss of catalytic activity due to the accumulation of reaction product residue is treated in a chemical conversion process reaction zone in the presence of feedstock(s) with ultrasonic energy of a magnitude and a duration sufficient to restore at least a significant percentage of the lost activity.

2 Claims, No Drawings

REACTIVATION OF PARTIALLY DEACTIVATED CATALYST EMPLOYING ULTRASONIC ENERGY

BACKGROUND OF THE INVENTION

This invention relates to catalyzed chemical conversion processes in which solid catalysts become deactivated through the accumulation of reaction product residue or other solid contaminant, e.g., "coke" or other carbonaceous residue, and in particular, to the reactivation of such catalysts using ultrasonic energy applied to the catalysts after they have become partially but less than completely deactivated due to such accumulated residue.

The use of solid catalysts to effect chemical conversion processes such as cracking, reforming, isomerization, disproportionation, alkylation, hydration, etherification, etc., is known. These catalysts include non-crystalline or amorphous types such as silica and alumina, and crystalline types such as the zeolites, both of which types can contain one or more other catalytically active species. In use, the catalysts gradually accumulate deposits, or residues, which cover the catalysts' surfaces and/or fill their pores eventually rendering them essentially completely inactive. Thus, at some point during their on-stream life, a period of time which can be just a few minutes in the case of a cracking operation to hours, days or even weeks in the case of some other types of chemical conversions, e.g., olefin hydration to produce alkanol, it becomes necessary to recover the catalysts and to reactivate them. One of the most commonly practiced catalyst reactivation procedures employs a burn-off procedure in which the residues are converted to gaseous carbon oxides and water.

Some types of solid catalysts, however, cannot withstand the high temperatures, generally from about 600° F. to about 1100° F., which are typical of the aforementioned burn-off reactivation procedures. One such catalyst, a boron trifluoride-graphite intercalate which is used in paraffin alkylation, undergoes irreversible damage when subjected to temperatures of this magnitude. Other thermally sensitive catalysts respond in much the same way to the high temperatures of oxidative burn-off operations.

U.S. Pat No. 4,086,184 describes the reactivation of hydrocarbon conversion catalysts employing ultrasonic sound, or insonation, either before or after a conventional burn-off operation. The reactivation procedure of this patent is disadvantageous in requiring separation of the catalyst from the feedstock, reactivating the catalyst and only then resuming the conversion operation. Even when, in accordance with this patent, the ultrasonic insonation is carried out within the conversion zone, i.e., within the reactor, the reactor must first be drained of feedstock and filled with a viscous liquid medium prior to insonation. This, of course, requires an interruption in the operation of the conversion process.

SUMMARY OF THE INVENTION

It is an object of the present invention to reactivate a solid catalyst which has become partially deactivated through the accumulation of reaction product residue and/or other contaminant(s) employing ultrasonic energy, preferably at a relatively low temperature in the case of thermally sensitive catalysts.

It is a particular object of the invention to reactivate such partially deactivated catalyst in a chemical conversion zone in the presence of feedstock, preferably without interruption of the chemical conversion operation.

It is another particular object of the invention to provide a process for preventing excessive accumulation of residue on solid catalyst while said catalysts are in use utilizing ultrasonic energy, thus prolonging the useful on-stream life of the catalysts and even dispensing entirely with the need to isolate them for purposes of off-stream reactivation.

It is a further particular object of the invention to subject a catalyst while on-stream to intermittent pulses of ultrasonic energy to prevent or retard the accumulation of catalyst-deactivating contaminant(s).

In accordance with the foregoing objects, in a catalyzed chemical conversion process employing a catalyst composition which undergoes a loss of activity due to accumulation of contaminant, an improvement is provided which comprises subjecting the catalyst after it has undergone a partial but less than complete loss of activity due to contaminant accumulation with ultrasonic energy within a chemical conversion zone in the presence of feedstock, the magnitude of such ultrasonic energy and its duration being sufficient to restore a substantial percentage of the lost activity of the catalyst.

The process of the present invention possesses several significant advantages over the ultrasonic insonation catalyst reactivation procedure disclosed in U.S. Pat. No. 4,086,184 discussed above. Unlike the procedure of the prior patent where the deactivated catalyst must be separated from the feedstock, the reactivation process herein is carried out in the presence of feedstock, preferably while the chemical conversion operation is in full progress. Another important advantage of the present invention over the reactivation process of U.S. Pat. No. 4,086,184 involves the timing of the ultrasonic treatment step. In the prior patent, insonation is carried out upon a catalyst which has become essentially fully deactivated, referred to in the patent as a "permanently" deactivated catalyst. As shown in all of the working examples of the patent, insonation is always accompanied by a conventional burn-off procedure, an apparent requirement for effective catalyst reactivation. In the process of the present invention, ultrasonic treatment is carried out upon a catalyst which has undergone only partial deactivation such that this treatment by itself and in the absence of any other reactivation treatment such as a burn-off operation will be effective to restore a substantial percentage of the lost catalyst activity.

DESCRIPTION OF THE PREFERRED EMBODIMENTS

The catalysts which can be reactivated in accordance with this invention include any of those disclosed in U.S. Pat. No. 4,086,184, supra, the contents of which are incorporated by reference herein. The catalysts disclosed in U.S. Pat. No. 4,086,184 are those which are useful in hydrocarbon conversion reactions, e.g., cracking, hydrocracking, reforming, hydroisomerization, alkylation, disproportionation, etc. According to the patent, the preferred catalyst composition comprises a mixture of a major amount of an amorphous component and a minor amount of a hydrogenation component preferably comprising one or more transitional metals selected from Groups VIB and/or VIII of the Periodic Table, e.g., molybdenum, chromium, tungsten, nickel, cobalt, palladium, iron, rhodium, and the like, as well as combinations of these metals and/or their oxides and/or sulfides. The amorphous component, i.e., the support, can be selected from any one of a large number of highly porous non-crystalline organic, and preferably inorganic, materials, e.g., metal and metal alloys, sintered glass, firebrick, diatomaceous earth, inorganic refractory oxides, organic resins such as polyesters, phenolics, etc., metal phosphates such as boron phosphate, calcium phosphate and zirconium phosphate, metal oxides such as iron sulfide and nickel sulfide, inorganic oxide gels, and the like. Also included as suitable catalysts are those containing a crystalline aluminosilicate, or zeolite, an amorphous component such as any of those aforementioned and a hydrogenation component. According to the patent, presentative examples of particularly preferred zeolites are zeolites X, Y, and L, faujasite and mordenite.

In addition to the foregoing catalysts, the reactivation process of the present invention is suitable for practice with any other catalysts which undergo deactivation through the accumulation of reaction product residues, e.g., "coke," coke precursors or other carbonaceous materials as well as any other types of contaminants which adhere to the surfaces of the catalysts, occlude their pores or otherwise reduce or prevent contact between feedstock(s) and active catalyst sites. Such catalysts embrace essentially all of the zeolites and zeolite-like materials including the medium pore varieties such as ZSM-5, ZSM-11, ZSM-5/ZSM-11 intermediates, ZSM-12, ZSM-23, ZSM-35, ZSM-38, ZSM-48 and the large pore zeolites such as the aforementioned zeolites X, Y and L, faujasite and mordenite as well as ZSM-3, ZSM-4, ZSM-18, ZSM-20 and zeolite beta.

While the reactivation process of the present invention can be practiced with any catalyst which is subject to deactivation through contaminant accumulation including catalysts which are relatively thermally stable, it is especially advantageous when practiced upon catalysts which cannot readily withstand the thermal stress of typical high temperature coke burn-off procedures, e.g., boron trifluoride graphite intercalate such as described in U.S. Pat. No. 3,984,352 and other graphite and layered inorganic compound intercalates, metal alkyls such as those of the Ziegler-Natta type, supported metal species such as platinum, palladium, rhodium or other noble metal species on carbon, alumina, zirconia or other inorganic support, resin catalysts, ion-exchange catalysts, and so forth.

While high temperature reactivation procedures can cause agglomeration of supported metal species with a consequent reduction in catalytic activity, the present ultrasonic reactivation process is effective even at relatively low temperatures and therefore can be carried out without causing any significant agglomeration of the metal species component when such catalysts are reactivated in accordance with this invention. Thus, the reactivation process herein is especially advantageous for use in reactivating catalysts whose metal species components are particularly prone to agglomeration at the high temperatures of conventional burn-off operations.

The chemical conversion processes utilizing these and other contaminant-accumulating catalysts which can benefit from the process of the present invention include all manner of hydrocarbon conversion processes utilizing one or more kinds of feedstock, methanol and/or dimethyl ether to gasoline conversions, olefin hydration and etherification conversion reactions, and so forth. The chemical conversions can be carried out continuously or in batch and in one or a series of interconnected chemical conversion zones employing fixed bed, moving bed and/or fluidized catalyst bed conditions.

More particularly, the chemical conversion processes which result in partially deactivated catalysts which can be reactivated in accordance with this invention include, as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 to about 20; dehydrogenating hydrocarbons with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g. benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g., dimethylether, or mixtures thereof to hydrocarbons including aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure of from about atmospheric to about 60 atmospheres and a weight hourly space velocity of from about 0.08 to about 20; alkylating aromatic hydrocarbons, e.g. benzene and alkylbenzenes, in the presence of an alkylating agent, e.g. olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1; alkylating isoparaffins containing from 4 to 20 carbon atoms with olefins containing from 2 to 12 carbon atoms under reaction conditions which include temperatures ranging from ambient up to 500° C. and pressure ranging from atmospheric up to 5000 psig; hydrating light olefins to provide alkanols and/or ethers, preferably under liquid phase or gas-liquid multi-phase conditions; and, reacting light olefins with lower alkanols to provide ethers at elevated temperature and pressure.

The expression "partially deactivated catalyst" refers to a catalyst which has undergone some degree of deactivation, however slight, and preferably at least about a 10, and still more preferably at least about a 20, percent loss in its catalytic activity relative to the activity of the fresh catalyst but no more than about a 75, and preferably no more than about a 60, percent loss in catalytic activity relative to the activity of the fresh catalyst, said loss of activity being measured in terms of the reduction in the percentage conversion of feedstock (or in the case of multiple feedstocks, the reduction in the percentage conversion of one of the feedstocks) for a given chemical conversion operation. It is also within the scope of the invention to periodically subject a catalyst to ultrasonic energy virtually from the inception of its on-stream use in order to avoid or lessen the accumulation of inactivating contaminant(s). In this way, the useful on-stream life of the catalyst can be considerably extended and the need for aggressive reactivation procedures such as burn-off can be eliminated or minimized.

The magnitude and duration of the ultrasonic treatment will ordinarily be sufficient to restore a substantial percentage of the lost activity of the catalyst, for example, at least about 20, preferably at least about 30, and still more preferably at least about 50, percent of the lost catalyst activity. The conditions of ultrasonic treatment required to achieve these levels of reactivation will, of course, vary according to the nature of the partially deactivated catalyst to be reactivated, the nature of the deactivating solid contaminant and the chemical conversion process involved. In general, as the ultrasonic energy level is increased, the duration of its application will decrease and, conversely, as the ultrasonic energy level is decreased, the duration of its application must be increased in order to achieve a comparable level of reactivation. Simple and routine testing can be followed to ascertain optimum levels of ultrasonic energy and treatment times for a given chemical conversion operation.

The frequencies of the ultrasonic energy contemplated herein lie in the range of from about 5,000 to about 500,000, and preferably from about 20,000 to about 50,000 Hz. Essentially any high energy sonic or ultrasonic energy device can be employed to accomplish the reactivation method of this invention. A preferred sonic energy device includes a sonic probe having a generator, converter, and transducer associated therewith which converts electricity to metal vibration through a piezoelectric magneto strictive device. A useful sonic agitation device is the Branson 3200 sonifier manufactured by Branson Sonic Power Company which, when coupled with a converter or transducer, produces vibrations with an associated metal horn. The power output of the transducer is advantageously in the range of from about 1 to about 50, and preferably from about 5 to about 40, watts per square inch. The transducer should be positioned relative to the contents of the chemical conversion zone as to transfer its acoustic energy to the particles of partially deactivated catalyst contained therein. In most cases, ultrasonic treatment of a partially deactivated catalyst within the foregoing frequency and power density ranges for a period of from about 3 to about 30, and preferably from 5 to about 25, minutes will be effective to recover the aforestated percentages of lost catalyst activity.

As previously noted, some of the advantages of the present catalyst reactivation method lie in the fact that there is no need to separate the partially deactivated catalyst from the feedstock(s) or subject the catalyst to a burn-off operation. Thus, the catalyst can be reactivated in situ, i.e., within the chemical conversion zone of the reactor and in the presence of feedstock(s) and even under ordinary chemical conversion conditions so that the catalyst remains on stream and the chemical conversion operation continues without interruption. If desired, however, the ultrasonic treatment of the partially deactivated catalyst can be carried out under conditions of temperature and/or pressure which differ from those employed in the chemical conversion process.

The following example illustrates the catalyst reactivation process herein for the reactivation of a partially deactivated boron trifluoride-graphite intercalate catalyst employed in an alkylation process in which isobutane is reacted with a mixture of cis/trans-2-butene to provide an octane alkylate. Similar results can be achieved by application of the catalyst reactivation process to other partially deactivated catalysts resulting from other chemical conversion operations.

EXAMPLE

Paraffin alkylation was carried out in a Parr reactor at 24° C. and 150 psig. The reactor contained 80 g isobutane and 4.0 g $BF_3$-graphite intercalate catalyst pretreated with 1.1. g anhydrous HF. A 1/1 mixture of cis/trans-2-butene was introduced into the reactor at 0.5 WHSV over 4 hours. The stirring rate was 1500 rpm. Product alkylate was withdrawn from the reactor. Butene conversion to alkylate was 100%.

The reactor containing the above catalyst was recharged with isobutane and the alkylation was repeated as above. The product was withdrawn from the reactor. Butene conversion decreased from 100% to 40% indicating a 60% loss of catalyst activity relative to the fresh catalyst.

The reactor was charged with 80 g isobutane and treated with ultrasound for 20 minutes at 25° C. using a Branson 3200 sonifier operating at a frequency of about 50,000 Hz and a power density of about 12 watts per square inch. The alkylation process was repeated as above. As a result of the ultrasonic treatment, butene conversion increased from 40% to 72%, a recovery of over 50% of the lost catalyst activity.

What is claimed is:

1. In a catalyzed alkylation process employing a solid boron-containing catalyst composition which undergoes a loss of activity due to accumulation of solid contaminant on the catalyst, the improvement which comprises subjecting the catalyst after it has undergone a partial but less than complete loss of activity due to solid contaminant accumulation with ultrasonic energy within a chemical conversion zone containing a liquid feedstock, the catalyst being present therein, the magnitude of such ultrasonic energy and its duration being sufficient to restore a substantial percentage of the lost activity of the catalyst, wherein said catalyst includes boron trifluoride.

2. The alkylation process of claim 1 wherein the solid boron-containing catalyst is a boron trifluoride-graphite intercalate.

* * * * *